US005735281A

United States Patent [19]
Rafter et al.

[11] Patent Number: 5,735,281
[45] Date of Patent: Apr. 7, 1998

[54] METHOD OF ENHANCING AND PROLONGING THE EFFECT OF ULTRASOUND CONTRAST AGENTS

[75] Inventors: Patrick G. Rafter, Woburn; Ronald D. Gatzke, Lexington; Alwyn P. D'Sa, Cambridge, all of Mass.

[73] Assignee: Hewlett-Packard Company, Palo Alto, Calif.

[21] Appl. No.: 695,267

[22] Filed: Aug. 9, 1996

[51] Int. Cl.$^6$ ..................................... A61B 8/00
[52] U.S. Cl. ..................................... 128/662.02
[58] Field of Search ............... 128/660.01, 660.07, 128/662.02; 424/9.1, 9.32, 9.321

[56] References Cited

U.S. PATENT DOCUMENTS 5,410,205  4/1995  Gururaja .................... 310/328
5,577,505  11/1996  Brock-Fisher et al. ........... 128/662.02

OTHER PUBLICATIONS

Circulation, vol. 92, No. 9, Nov. 1, 1995 Transient Mycardial Contrast After Initial Exposure to Diagnostic Ultrasound Pressures With Minute Doses of Intravenously Injected Microbubbles Thomas R. Porter, MD; Feng Xie, MD/pp. 2391–2395.

*Primary Examiner*—George Manuel
*Attorney, Agent, or Firm*—Pamela Lau Kee

[57] ABSTRACT

Ultrasound energy has been observed to rapidly destroy a large quantity of microbubbles. The duration and intensity of the contrast effect is greatly diminished by conventional imaging frame rates and power levels. Altering the imaging sequence by strategically shooting ultrasound image frames at various transmit powers and reducing the number of transmit lines per frame allows for enhancement of the contrast effect (increasing maximum intensity and duration).

20 Claims, 13 Drawing Sheets

METHOD OF ENHANCING AND PROLONGING THE EFFECT OF ULTRASOUND CONTRAST AGENTS

FIELD OF THE INVENTION

This invention pertains to ultrasound imaging systems. In particular, this invention is directed towards increasing sensitivity in the detection of responses from ultrasound contrast agents.

BACKGROUND OF THE INVENTION

Medical ultrasound imaging systems have been designed under the premise that the impinging ultrasonic energy produces a linear response. In order to be linear, a system must obey the following equation;

IF x1(t)=a system input and y1(t) is the corresponding output and x2(t)=a system input and y2(t) is the corresponding output

THEN $(a*x1(t)+b*x2(t))$ as an input gives $(a*y1(t)+b*y2(t))$ as an output

Current trends in research concentrate on investigating non-linear responses to ultrasonic energy. For example, some contrast agents have been found to provide a second harmonic response to impinging ultrasound energy at the fundamental excitation frequency, and this energy can be used to provide increased diagnostic information about the surrounding tissues. A second harmonic response occurs when an agent under increasing ultrasonic pressure, "maps" energy into the harmonics of the fundamental frequency, in addition to the fundamental. Recently, it has been discovered that when microbubble based contrast agents resonate they are destroyed.

In one prior art diagnostic system, disclosed by Johnson et al. in U.S. Pat. No. 5,456,257, the presence of coated microbubble contrast agents in the body of a patient is detected by transmitting ultrasonic energy which causes the destruction of the microbubble. The diagnostic system detects the microbubble destruction through phase insensitive detection and differentiation of echoes received from consecutive ultrasonic transmission.

It would be desirable to design frame sequencing techniques which improve sensitivity of bubble detection and allow prolonged enhancement of the contrast effect by minimizing bubble destruction.

SUMMARY OF THE INVENTION

Ultrasound energy has been observed to rapidly destroy a large quantity of microbubbles. The duration and intensity of the contrast effect is greatly diminished by conventional imaging frame rates and power levels. Altering the imaging sequence by strategically shooting ultrasound image flames at various transmit powers and reducing the number of transmit lines per frame allows for enhancement of the contrast effect (increasing maximum intensity and duration). It may be desirable to trigger the frame sequence off of the ECG signal because blood flow and backscatter vary throughout the cardiac cycle. Alternatively, it may be desirable to have the sequence triggered off of the ECG and gated by the respiration signal to compensate for the respiratory motion of the heart and the variation of cardiac blood flow with respiration. These sequences would apply to Color Doppler, Power Doppler, or 2D imaging techniques.

DETAILED DESCRIPTION OF THE PREFERRED EMBODIMENTS

Contrast agents resonate in the presence of an ultrasound field and the received signal can be detected by today's ultrasound scanners. It has been observed that higher transit powers increase the backscattering cross section of the microbubbles, particularly in harmonic mode, and they therefore scatter a larger portion of the impinging ultrasound signal. However, the duration of the contrast effect is shorter at high power levels, probably due to increased microbubble destruction and the subsequent lower concentrations. Different imaging sequences can be used to optimize this contrast effect.

Current ultrasound scanners transmit approximately 30 frames per second for dynamic visualization of anatomical structures in real time. The frame rate varies depending on imaging depth, number of transmit lines per frame, and imaging frequency. When imaging with contrast agents, it may be better to transmit a high-power frame followed by a series of low-power frames. The low-power frames will allow real time imaging while prolonging the contrast effect and the high-power frames will cause an increase in the contrast agent-to-tissue (signal-to-noise) ratio.

Synchronizing the imaging sequence to the patient's ECG allows a series of high-power frames to be strategically obtained. These frames may be fired at the same point of the heart cycle or at different points to allow for the piecing together of a complete heart cycle from multiple heart cycles using cine-loop technology. Minimizing high-power frames will allow for prolonged contrast effect thereby making endocardial border detection easier for ejection fraction and volume calculations as well as wall motion analysis. Simultaneously, the high-power frames make measurement of myocardial perfusion and critical timing parameters, such as wash-in and wash-out of contrast, possible. Gating off of a respiration signal will help minimize artifacts resulting from heart movement caused by patient breathing from heart cycle to heart cycle. As an option, the sequence may be accomplished with a mix of fundamental imaging and harmonic imaging. For example, it may be best to transmit the high-power frames in harmonic mode and the low-power frames in fundamental mode. These sequences are applicable across all ultrasound imaging modalities—2D imaging, Color Flow, Power Doppler Imaging, Doppler tissue colorization, etc.

Additionally, limiting the number of transmit lines may increase and prolong the contrast effect as well. Typically each ultrasound image frame is made up of 100 or more transmit lines which are steered at different angles. If fewer lines were transmitted it would be possible to use parallel processing on the receive path to fill an image. Combining this with the imaging sequences discussed will provide an even longer contrast effect.

Figure 1:
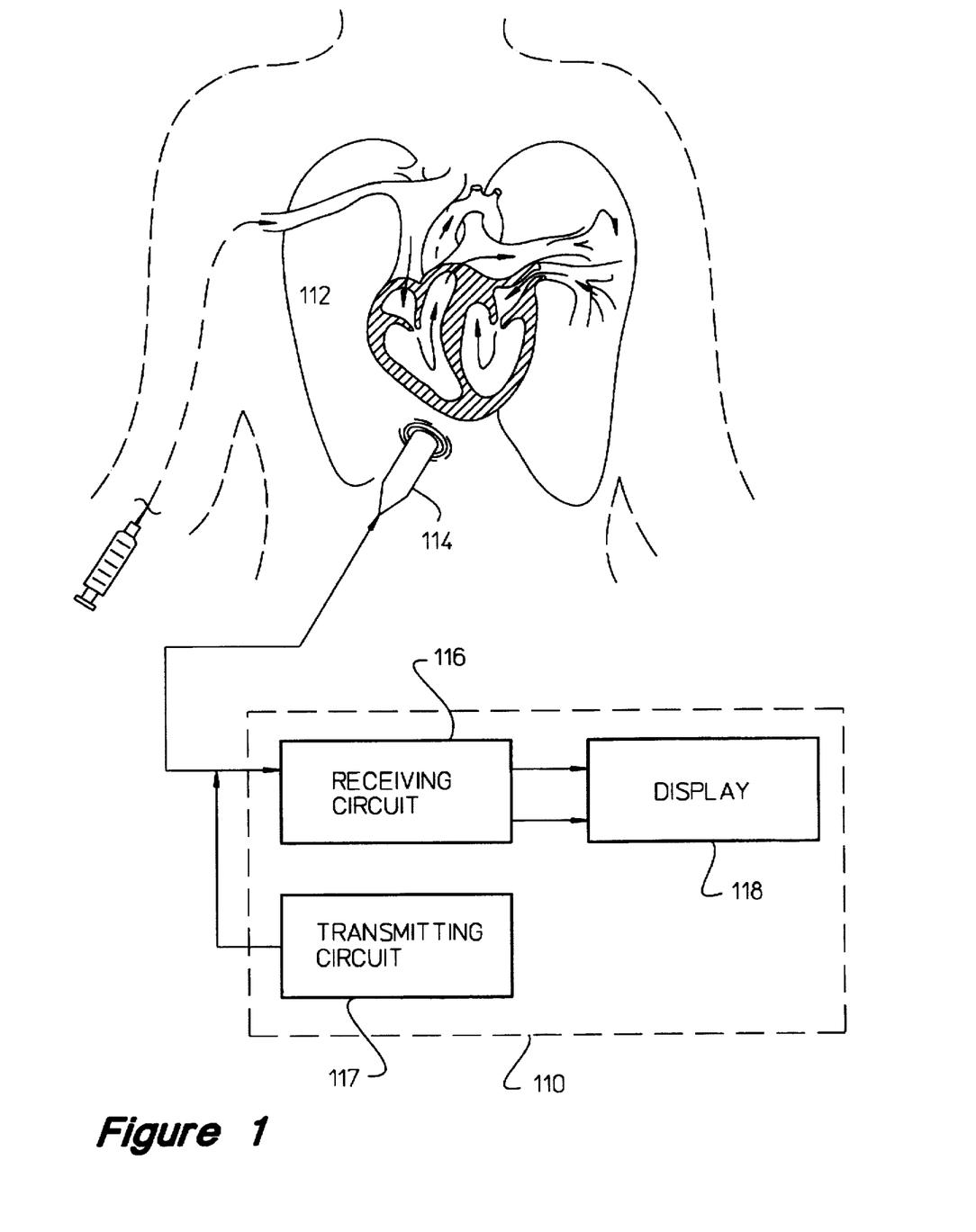
FIG. 1 illustrates a functional block diagram for an ultrasound imaging machine.

FIG. 1 illustrates a functional block diagram of an ultrasound imaging machine 110. An ultrasound probe 114 is connected to a receiving circuit 116 and a transmitting circuit 117. The receiving circuit 116 is further connected to a display 118.

In operation, contrast agent is injected into a patient's bloodstream, such as the superior vena cava. The contrast agent improves the blood pool backscatter relative to the tissue. The blood is black and the tissue is white. As described in the present invention, ultrasound image energy is applied to the heart 112 via the ultrasound probe 114. The received images may be used characterize the cardiac blood flow of the patient.

Figure 2:
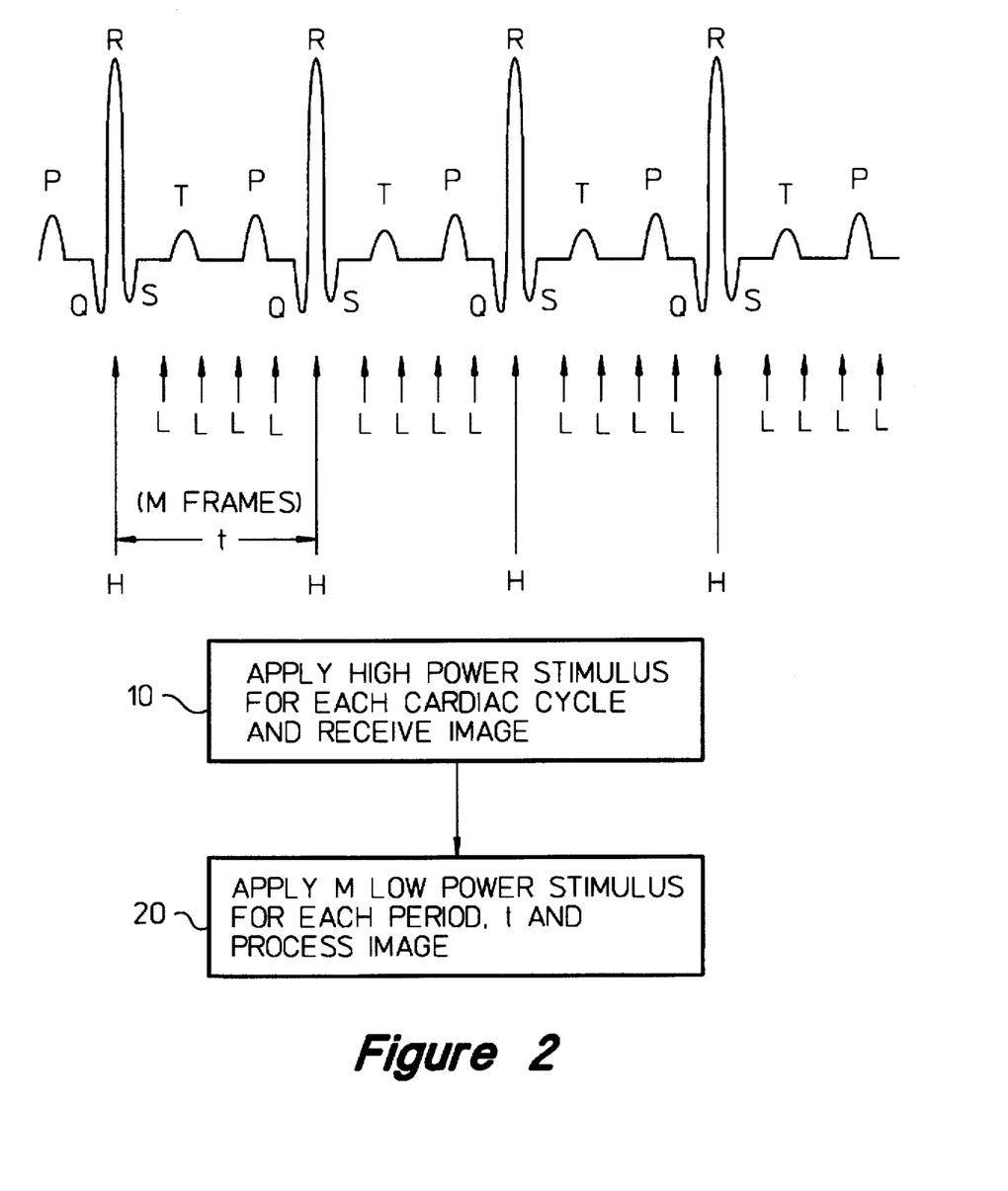
FIG. 2 illustrates a process flowchart in time for the method.

FIG. 2 illustrates a time process flowchart for the method. In step 10, one high power frame per cycle is shot and the image is gathered. The high power frame is optionally triggered off of the ECG waveform or triggered off of the ECG and further gated by the respiration waveform. In step 20, M (M>=0) low power frames are shot in between high power frames. The high power frames may be processed separately and stored in a cine loop.

Figure 3:
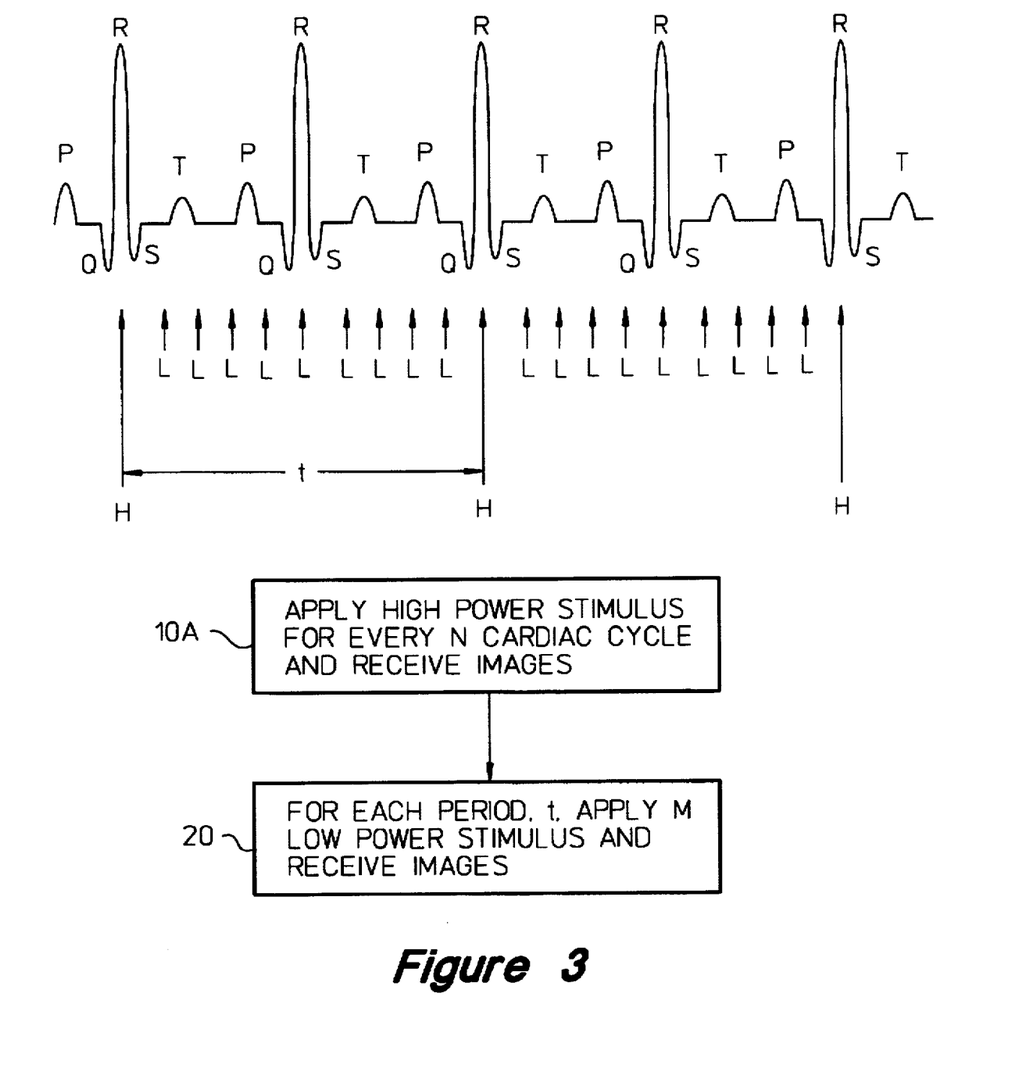
FIG. 3 illustrates a variation of the flowchart shown in FIG. 2.
Figure 4:
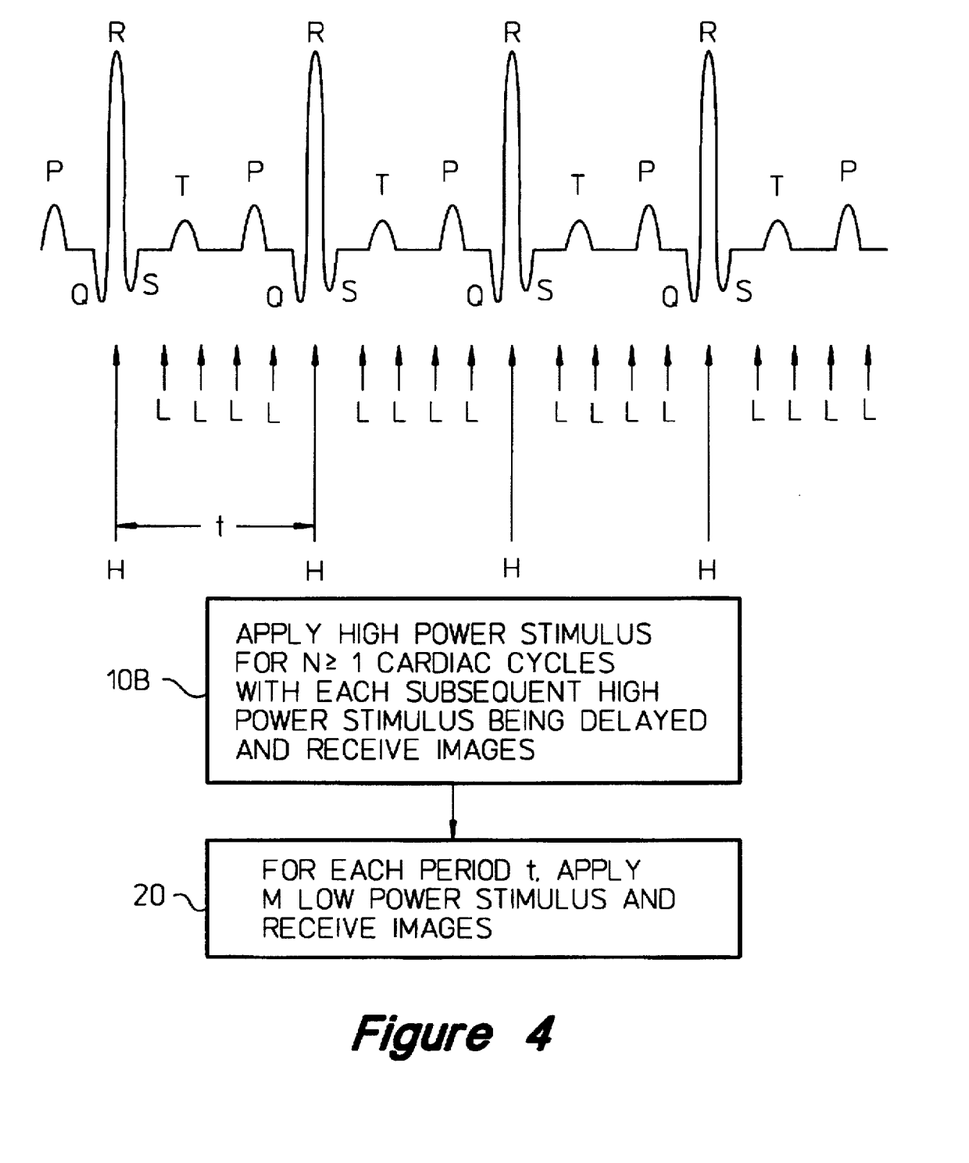
FIG. 4 illustrates a variation of the flowchart shown in FIG. 2.

FIG. 3 illustrates a variation of the process flowchart shown in FIG. 2. In step 10A, one high power frame is shot every N cycles (N>=1). FIG. 4 illustrates another variation of the process flowchart shown in FIG. 2. In step 10B, one high power frame is shot per N (N>=1) heart cycles with each subsequent high power frame increasingly delayed relative to an ECG trigger (i.e., R-wave). Also, triggering off of the ECG with respiration gating is desirable to reduce lung artifact and heart motion due to breathing.

Figure 5:
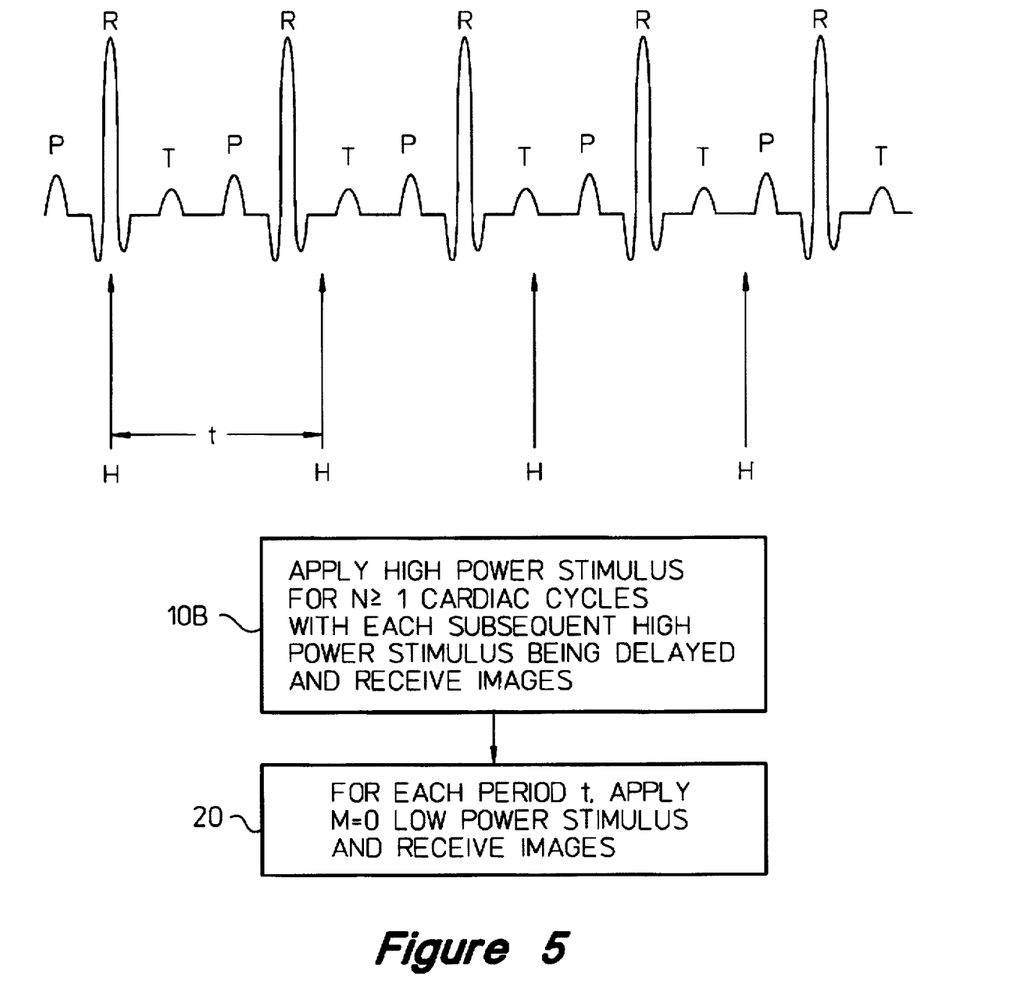
FIG. 5 illustrates a variation of the flowchart shown in FIG. 2.

FIG. 5 illustrates another variation of the process flowchart shown in FIG. 2. In step 10B, one high power frame is shot per N (N>=1) cardiac cycles with each frame incrementally delayed from an EGG trigger (i.e., R-wave). Alternatively, the frames can be delayed from an ECG trigger and gated by respiration. This is a special case of FIG. 3 without the low power frames.

Figure 6:
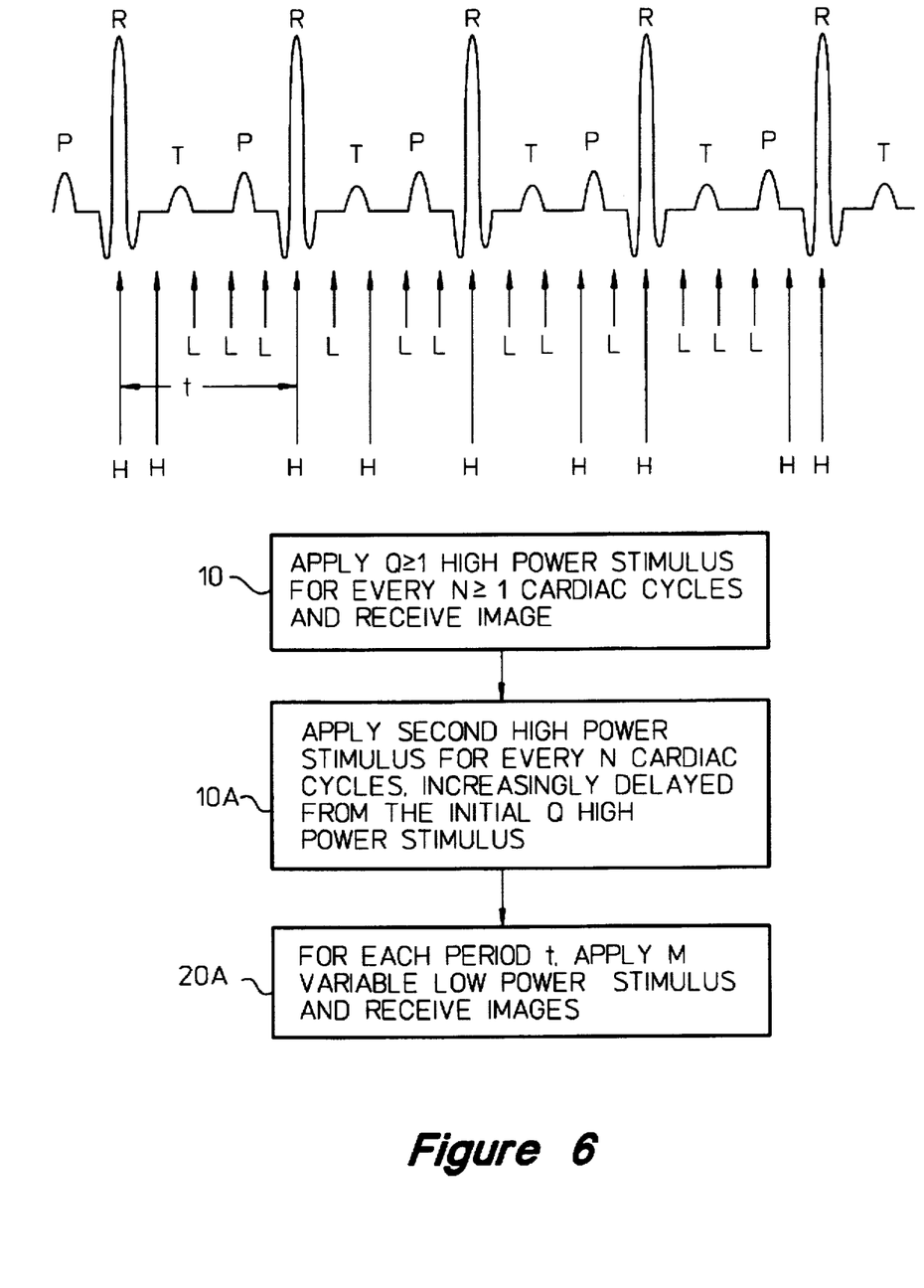
FIG. 6 illustrates a variation of the flowchart shown in FIG. 2.

FIG. 6 illustrates another variation of the process flowchart shown in FIG. 2. This is a combination of the methods disclosed in FIGS. 2 and 4. It is possible that flow can be measured from this method. The high power frames which are fired at the same point in the cardiac cycle every N cycles (N>=1) are used to destroy the contrast agent. The second high power frame, shot every N (N>=1) cycles, but not necessarily the same cycle as the first high power frame, then measures the amount of contrast agent which has returned since the first high power frame. This sequence can give an indication of myocardial (or other organ) blood flow.

Figure 7:
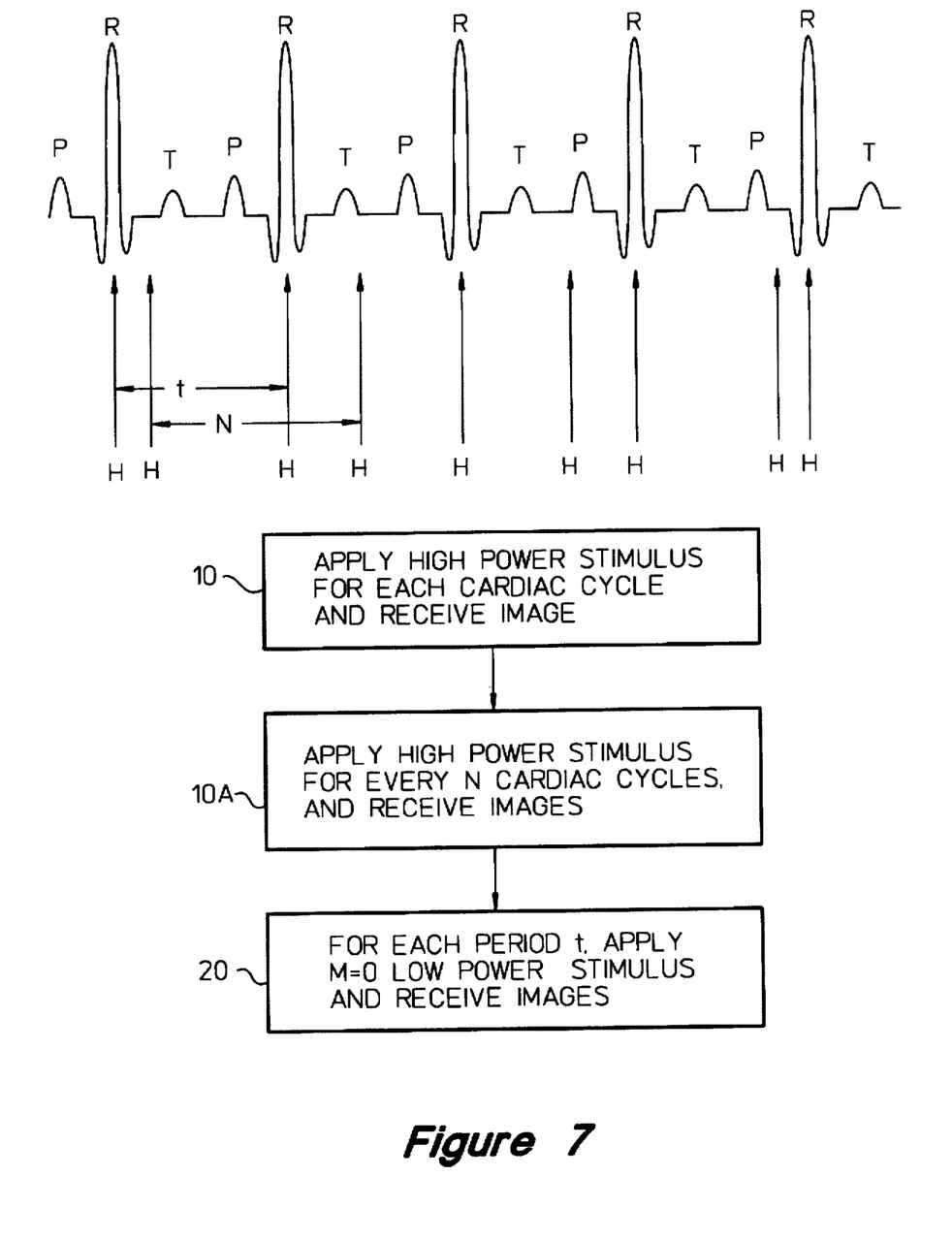
FIG. 7 illustrates a variation of the flowchart shown in FIG. 6.

FIG. 7 is a special case of FIG. 6 where only high power frames are shot.

Figure 8:
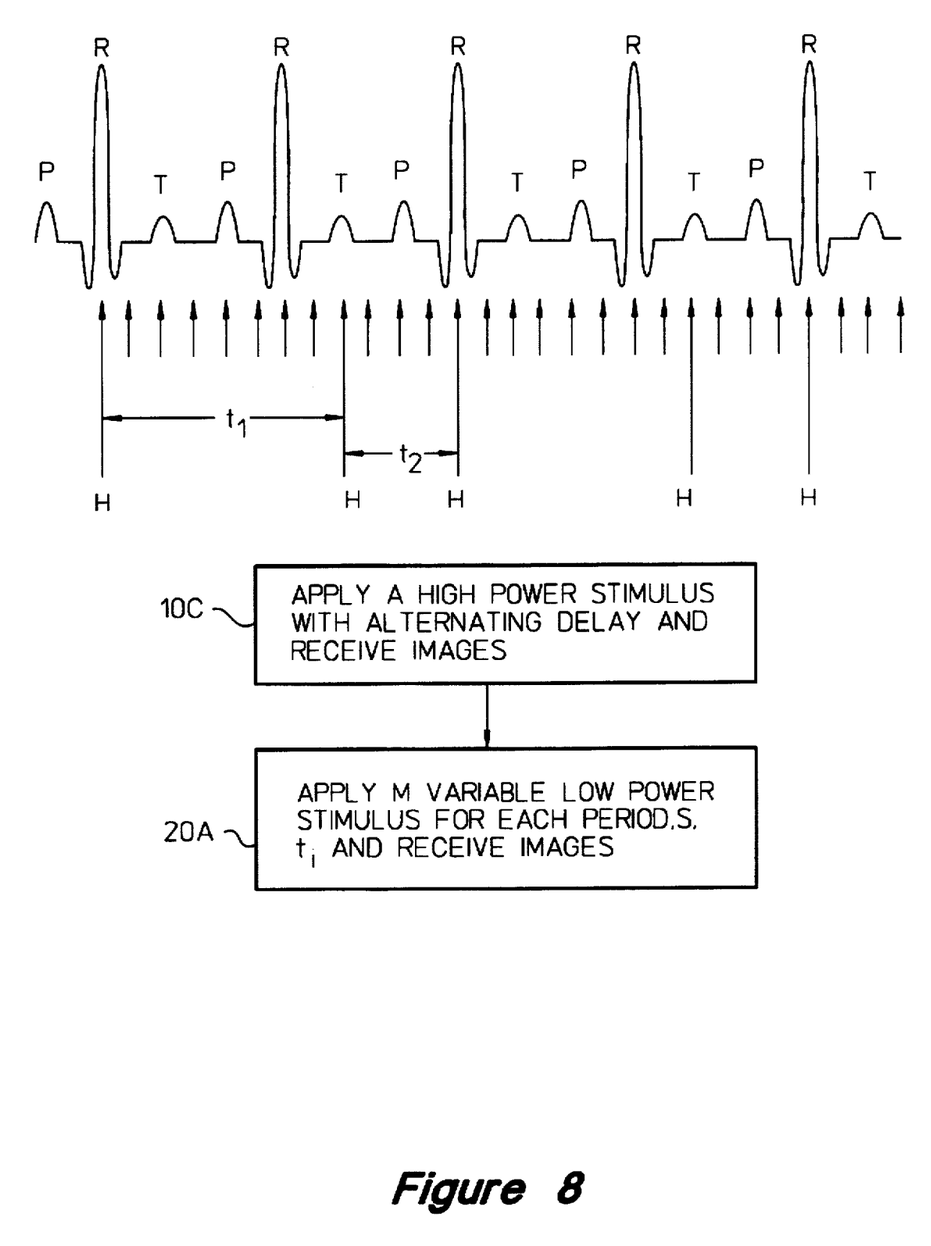
FIG. 8 illustrates a variation of the flowchart shown in FIG. 2 and FIG. 3.

FIG. 8 illustrates a variation of FIGS. 2 and 3. In step 10C, one high power frame is shot per N (N>=1) cycles with an alternating delay (i.e., systole one cycle, diastole the next). In step 20A, M (M>=0) variable low power frames are shot in between the high power frames. The frames are either synchronized off of the ECG or triggered off of the ECG and gated by the respiration signals.

Figure 9:
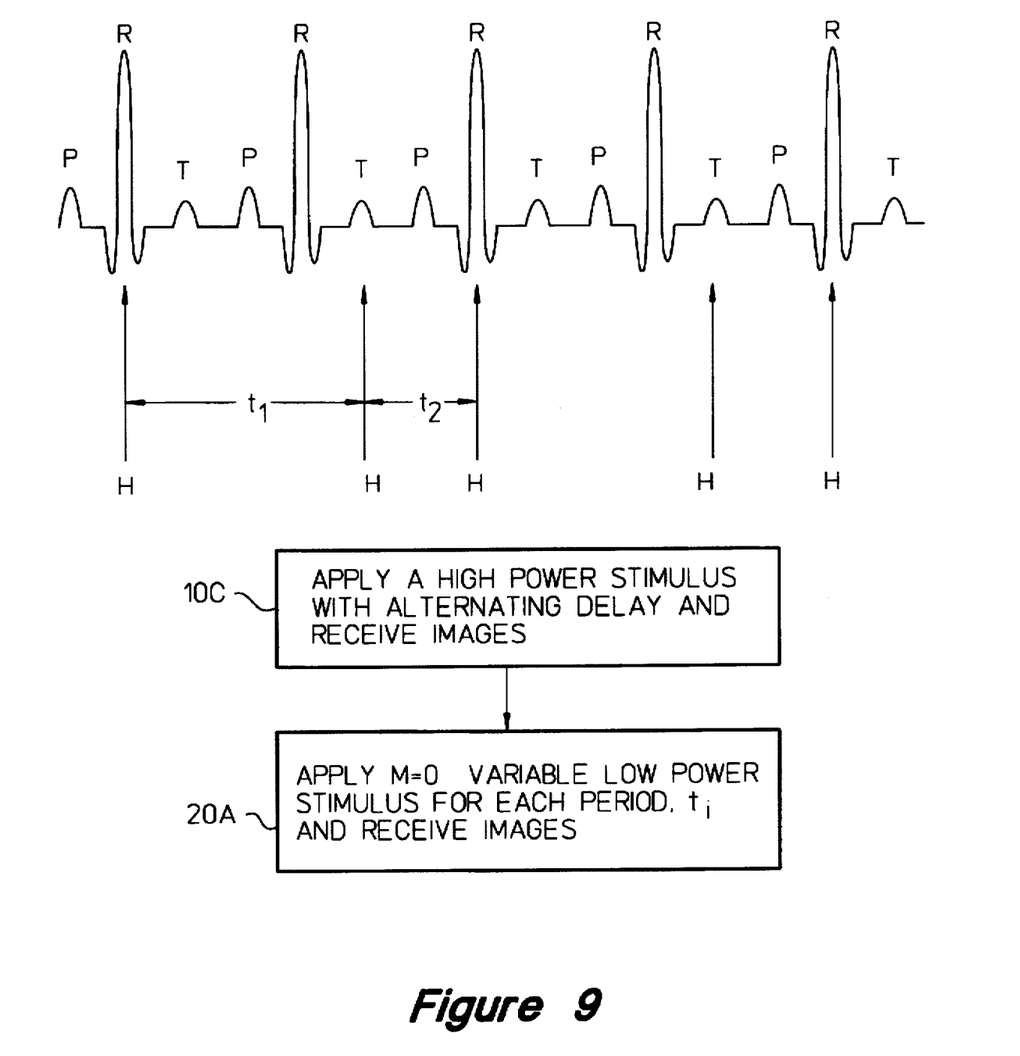
FIG. 9 illustrates a variation of the flowchart shown in FIG. 8.

FIG. 9 illustrates a variation of FIG. 8, with no low power frames being shot.

Figure 10:
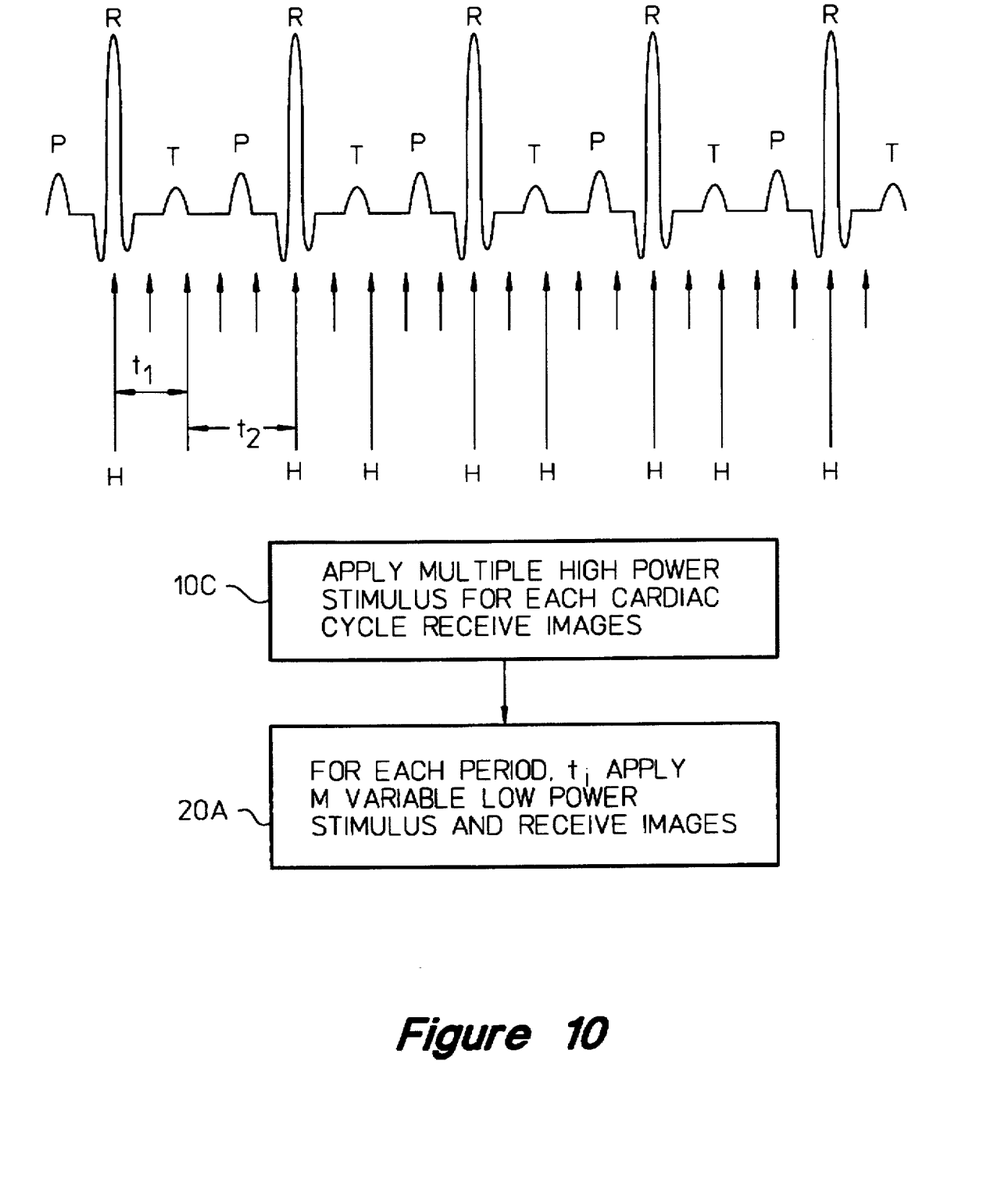
FIG. 10 illustrates a variation of the flowchart shown in FIG. 2.

FIG. 10 illustrates a variation of FIG. 2. Q (Q>=1) high power frames are shot per cardiac cycle with M (M>=0) variable low power frames shot in between the high power frames. The sequence is once again synchronized off of the ECG or ECG and gated by respiration.

Figure 11:
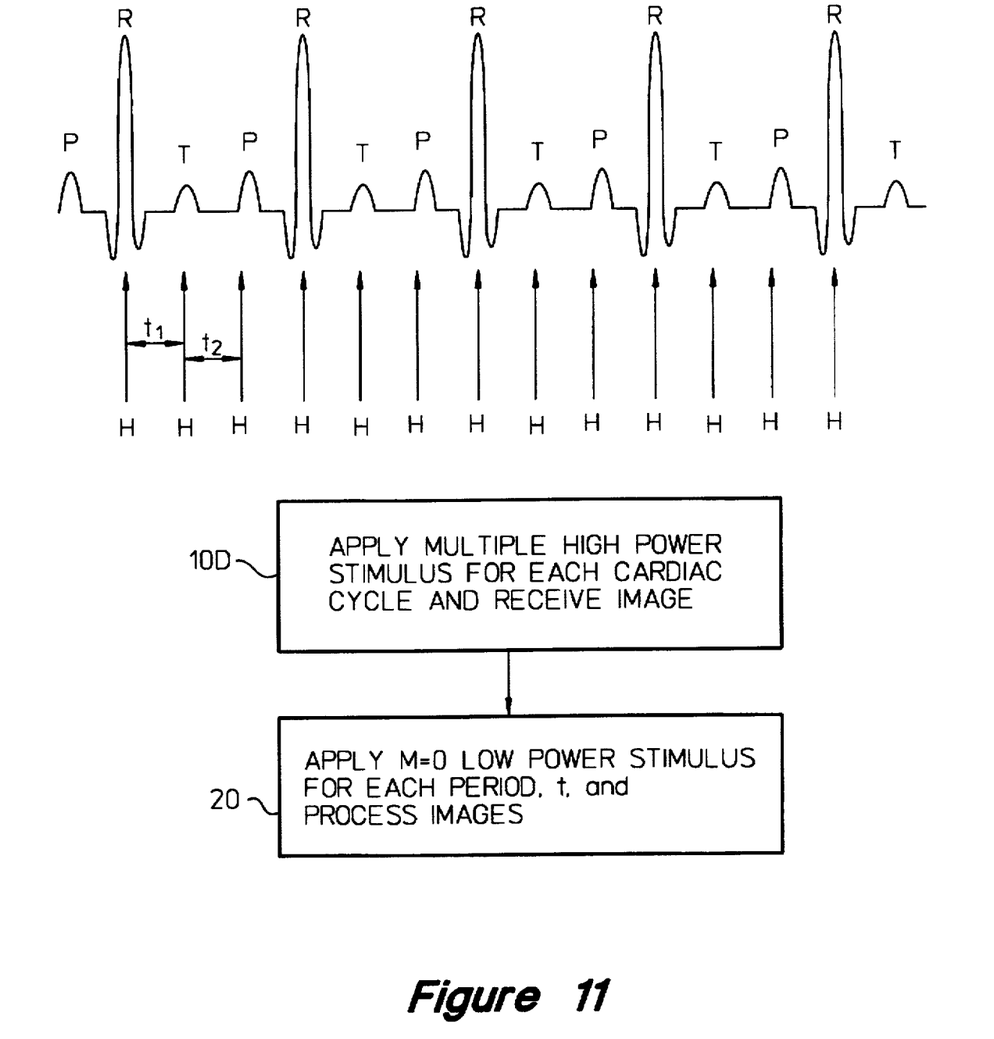
FIG. 11 illustrates a variation of the flowchart shown in FIG. 2.

FIG. 11 illustrates a variation of FIG. 2. Q (Q>=1) high power frames are shot per heart cycle. This is an ECG synchronized frame rate control. Optionally, an unsynchronized frame rate control could be used with contrast agents, allowing dial-back from standard 30 Hz imaging.

Figure 12:
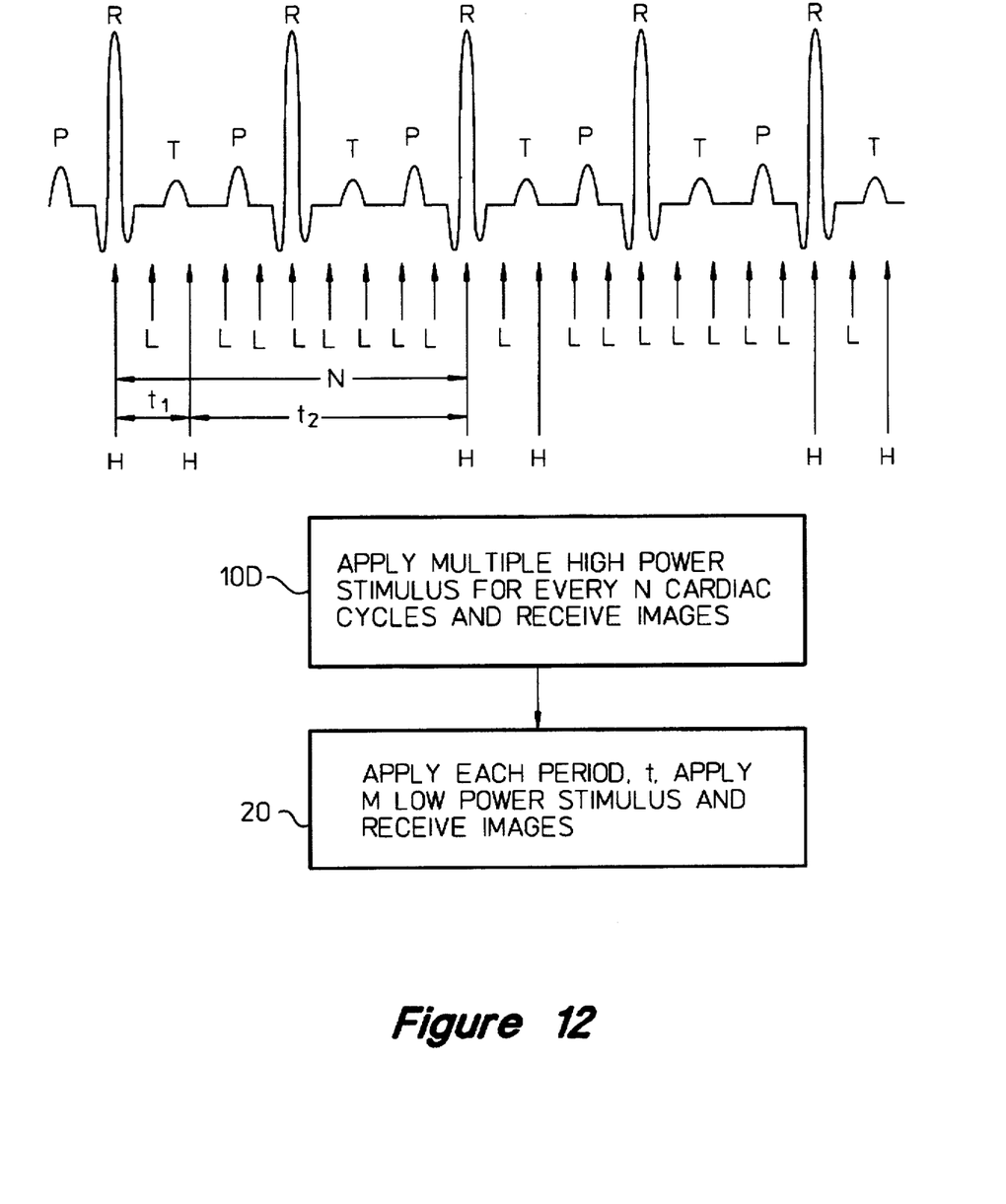
FIG. 12 illustrates a variation of the flowchart shown in FIG. 10.

FIG. 12 is variation of FIG. 10. Q (Q>=1) high power frames are shot per cycle repeating every N (N>=1) heart cycles with a variable amount of low power frames shot in between. This sequence is triggered off of the ECG or the ECG gated by respiration.

Figure 13:
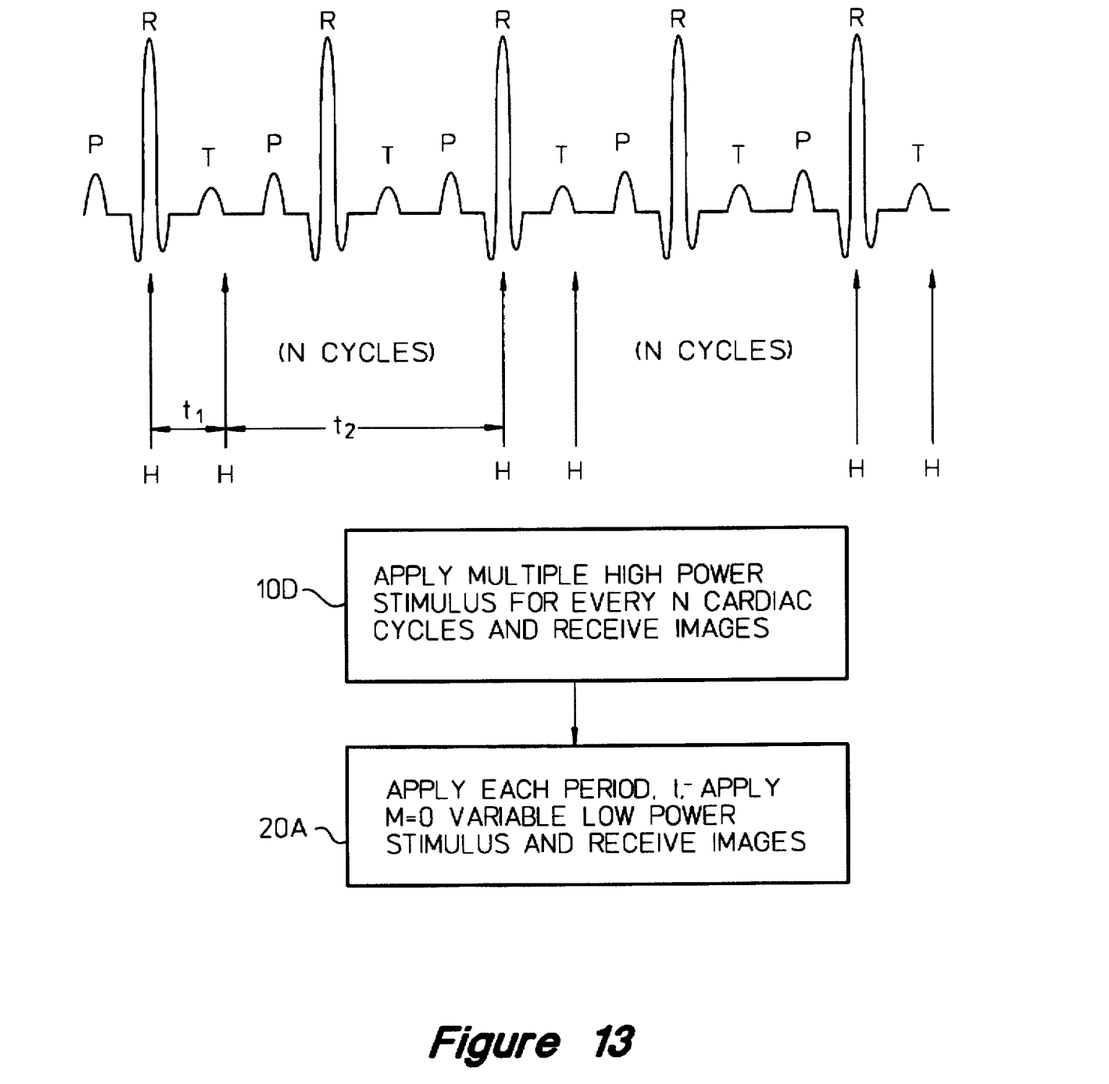
FIG. 13 illustrates a variation of the flowchart shown in FIG. 12.

FIG. 13 is a variation of FIG. 12 with the low power frames not fired. Q (Q>=1) high power frames are shot per cycle repeating every N (N>=1) cycles.

We claim:

1. A method for enhancing and prolonging the effect of ultrasound contrast agents comprising the steps of:
    introducing an ultrasound contrast agent into a patient;
    applying a high power stimulus each period to generate a high power stimulus image;
    receiving and processing the high power stimulus image;
    applying M (M≧0) low power stimuli each period to generate multiple low power stimulus images; and
    receiving and processing the multiple low power stimulus images.

2. A method of enhancing and prolonging the effect of ultrasound contrast agents, as defined in claim 1, wherein the high power stimulus begins each period.

3. A method of enhancing and prolonging the effect of ultrasound contrast agents, as defined in claim 2, wherein the high power stimulus is synchronized to the patient's EGG and the period duration is N (N≧1) cardiac cycles.

4. A method of enhancing and prolonging the effect of ultrasound contrast agents, as defined in claim 3, wherein the period is gated by the respiration signal of the patient.

5. A method of enhancing and prolonging the effect of ultrasound contrast agents, as defined in claim 2, wherein each subsequent period is incrementally delayed from an EGG synchronized trigger and the trigger occurs every N (N≧1) cardiac cycles.

6. A method of enhancing and prolonging the effect of ultrasound contrast agents, as defined in claim 5, wherein the EGG synchronized trigger is further gated off the patient's respiration signal.

7. A method of enhancing and prolonging the effect of ultrasound contrast agents, as defined in claim 2, wherein a series of periods is synchronized to an EGG based trigger and the trigger occurs every N (N≧1) cardiac cycles.

8. A method of enhancing and prolonging the effect of ultrasound contrast agents, as defined in claim 7, wherein each period duration is a fixed fractional number of cardiac cycles for the series.

9. A method of enhancing and prolonging the effect of ultrasound contrast agents, as defined in claim 8, wherein the series is further gated by a respiration signal.

10. A method enhancing and prolonging the effect of ultrasound contrast agents, as defined in claim 9, wherein N=1 cardiac cycle.

11. A method enhancing and prolonging the effect of ultrasound contrast agents, as defined in claim 10, wherein the number of low power frames, M=0.

12. A method enhancing and prolonging the effect of ultrasound contrast agents, as defined in claim 8, wherein the series consists of two periods, with one period beginning at end-diastole and the second period beginning at end systole.

13. A method enhancing and prolonging the effect of ultrasound contrast agents, as defined in claim 8, wherein N=1 cardiac cycles.

14. A method enhancing and prolonging the effect of ultrasound contrast agents, as defined in claim 13, wherein the number of low power frames, M=0.

15. A method enhancing and prolonging the effect of ultrasound contrast agents, as defined in claim 1, wherein the low power stimulus is $\geq 3$ dB down from the high power stimulus.

16. A method enhancing and prolonging the effect of ultrasound contrast agents comprising the steps of:
 introducing an ultrasound contrast agent into a patient;
 applying Q ($Q \geq 1$) high power stimuli each period to destroy the contrast agent and to generate multiple high power stimulus baseline images;
 receiving and processing the multiple high power stimulus baseline images;
 applying M ($M \geq 0$) low power stimuli each period to generate multiple low power stimulus images;
 receiving and processing the multiple low power stimulus images;
 applying an additional high power stimulus in the same period which is delayed relative to the Q high power stimuli;
 receiving and processing the second high power stimulus image;
 applying a second group of S ($S \geq 0$) low power stimuli each period to generate multiple low power stimulus images; and
 receiving and processing the multiple low power stimulus images.

17. A method enhancing and prolonging the effect of ultrasound contrast agents, as defined in claim 16, wherein a period is a sequence beginning with Q ($Q \geq 1$) multiple high power stimuli followed by M ($M \geq 0$) low power stimuli, subsequently followed by one high power stimulus, and ending with S ($S \geq 0$) low power stimuli, with the period synchronized to a specific point of the ECG and having a duration of N ($N \geq 1$) cardiac cycles and wherein a stimulus is a group of transit lines forming an image.

18. A method enhancing and prolonging the effect of ultrasound contrast agents, as defined in claim 17, wherein the second high power stimulus is incrementally delayed relative to the first Q high power stimuli.

19. A method enhancing and prolonging the effect of ultrasound contrast agents, as defined in claim 18, wherein the sequence is further gated by a respiration signal.

20. A method enhancing and prolonging the effect of ultrasound contrast agents, as defined in claim 18, wherein the low power stimulus is $\geq 3$ dB down from the high power stimulus.

* * * * *